US011524142B2

(12) United States Patent
Buller et al.

(10) Patent No.: US 11,524,142 B2
(45) Date of Patent: Dec. 13, 2022

(54) GUIDE EXTENSION CATHETER

(71) Applicant: Teleflex Life Sciences Limited, Valletta (MT)

(72) Inventors: Christopher E. Buller, Toronto (CA); Joshua Brenizer, Oak Grove, MN (US); Dean Peterson, Minneapolis, MN (US); Loic Van Horne, Minneapolis, MN (US)

(73) Assignee: Teleflex Life Sciences Limited, Valletta (MT)

( * ) Notice: Subject to any disclaimer, the term of this patent is extended or adjusted under 35 U.S.C. 154(b) by 547 days.

(21) Appl. No.: 16/644,321

(22) PCT Filed: Oct. 30, 2019

(86) PCT No.: PCT/US2019/058783
§ 371 (c)(1),
(2) Date: Mar. 4, 2020

(87) PCT Pub. No.: WO2020/112293
PCT Pub. Date: Jun. 4, 2020

(65) Prior Publication Data
US 2021/0008342 A1  Jan. 14, 2021

Related U.S. Application Data

(60) Provisional application No. 62/771,658, filed on Nov. 27, 2018.

(51) Int. Cl.
*A61M 25/01* (2006.01)
*A61M 39/06* (2006.01)
*A61M 25/02* (2006.01)

(52) U.S. Cl.
CPC .... *A61M 25/0138* (2013.01); *A61M 25/0102* (2013.01); *A61M 39/06* (2013.01); *A61M 2025/024* (2013.01); *A61M 2210/125* (2013.01)

(58) Field of Classification Search
CPC .......... A61M 25/0138; A61M 25/0102; A61M 39/06; A61M 2025/024; A61M 2210/125;
(Continued)

(56) References Cited

U.S. PATENT DOCUMENTS 4,000,739 A  1/1977  Stevens
4,166,468 A  9/1979  Haynie
(Continued)

FOREIGN PATENT DOCUMENTS

CA  2008784 C  7/2002
DE  69928825  7/2006
(Continued)

OTHER PUBLICATIONS

European Extended Search Report dated Jun. 22, 2022, in EP Application No. 22165689.5.
(Continued)

*Primary Examiner* — Amber R Stiles
(74) *Attorney, Agent, or Firm* — Gregory W. Smock

(57) ABSTRACT

Guide extension catheters and related methods are disclosed. A guide extension catheter can comprise an elongate tube member, a push member, and an external manipulation member. The push member can be eccentrically coupled relative to the tube member and extend proximally therefrom for slidably positioning the tube member within and partially beyond a distal end of a guide catheter. The manipulation member can be coupled to a proximal end of the push member, where the manipulation member can be configured to secure the guide extension catheter in place (Continued)

during use by attaching to an external object such that the tube member and push member remain stationary without user engagement.

20 Claims, 8 Drawing Sheets

(58) Field of Classification Search
CPC .... A61M 25/0662; A61M 2025/09125; A61B 2017/22044; A61B 2017/22094
See application file for complete search history.

(56) References Cited

U.S. PATENT DOCUMENTS

| | | |
|---|---|---|
| 4,289,128 A | 9/1981 | Rusch |
| 4,662,871 A | 5/1987 | Rafelson |
| 4,723,936 A | 2/1988 | Buchbinder et al. |
| 4,762,129 A | 8/1988 | Bonzel |
| 4,813,930 A | 3/1989 | Elliott |
| 4,832,028 A | 5/1989 | Patel |
| 4,838,268 A | 6/1989 | Keith et al. |
| 4,838,269 A | 6/1989 | Robinson et al. |
| 4,909,252 A | 3/1990 | Goldberger |
| 4,921,483 A | 5/1990 | Wijay et al. |
| 4,932,413 A | 6/1990 | Shockey et al. |
| 4,943,278 A | 7/1990 | Euteneuer et al. |
| 4,946,440 A | 8/1990 | Hall |
| 4,994,745 A | 2/1991 | Mizuta |
| 5,002,531 A | 3/1991 | Bonzel |
| 5,040,548 A | 8/1991 | Yock |
| 5,061,273 A | 10/1991 | Vock |
| 5,074,845 A | 12/1991 | Miraki et al. |
| 5,098,412 A | 3/1992 | Shiu |
| 5,102,403 A | 4/1992 | Alt |
| 5,120,323 A | 6/1992 | Shockey et al. |
| 5,122,125 A | 6/1992 | Deuss |
| 5,156,594 A | 10/1992 | Keith |
| 5,232,445 A | 8/1993 | Bonzel |
| 5,234,416 A | 8/1993 | Macaulay et al. |
| 5,257,974 A | 11/1993 | Cox |
| 5,267,958 A | 12/1993 | Buchbinder et al. |
| 5,290,247 A | 3/1994 | Crittenden |
| 5,328,472 A | 7/1994 | Steinke et al. |
| 5,350,395 A | 9/1994 | Yock |
| 5,368,567 A | 11/1994 | Lee |
| 5,383,853 A | 1/1995 | Jung et al. |
| 5,413,560 A | 5/1995 | Solar |
| 5,415,639 A | 5/1995 | VandenEinde et al. |
| 5,439,445 A | 8/1995 | Kontos |
| 5,441,489 A | 8/1995 | Utsumi et al. |
| 5,445,624 A | 8/1995 | Jimenez |
| 5,445,625 A | 8/1995 | Voda |
| 5,451,209 A | 9/1995 | Ainsworth et al. |
| 5,472,425 A | 12/1995 | Teirstein |
| 5,489,278 A | 2/1996 | Abrahamson |
| 5,527,292 A | 6/1996 | Adams et al. |
| 5,531,721 A | 7/1996 | Pepin et al. |
| 5,545,149 A | 8/1996 | Brin et al. |
| 5,549,553 A | 8/1996 | Ressemann et al. |
| 5,562,620 A | 10/1996 | Klein et al. |
| 5,567,203 A | 10/1996 | Euteneuer et al. |
| 5,571,087 A | 11/1996 | Ressemann et al. |
| 5,578,009 A | 11/1996 | Kraus et al. |
| 5,599,326 A | 2/1997 | Carter |
| 5,620,417 A | 4/1997 | Jang et al. |
| 5,649,909 A | 7/1997 | Cornelius |
| 5,658,263 A | 8/1997 | Dang et al. |
| 5,690,613 A | 11/1997 | Verbeek |
| 5,704,926 A | 1/1998 | Sutton |
| 5,720,300 A | 2/1998 | Fagan et al. |
| 5,720,724 A | 2/1998 | Ressemann et al. |
| 5,743,876 A | 4/1998 | Swanson |
| 5,772,642 A | 6/1998 | Ciamacco et al. |
| 5,776,141 A | 7/1998 | Klein et al. |
| 5,785,685 A | 7/1998 | Kugler et al. |
| 5,792,124 A | 8/1998 | Horrigan et al. |
| 5,843,022 A | 12/1998 | Willard et al. |
| 5,860,963 A | 1/1999 | Azam et al. |
| 5,891,056 A | 4/1999 | Ramzipoor |
| 5,902,290 A | 5/1999 | Peacock et al. |
| 5,911,715 A | 6/1999 | Berg et al. |
| 5,961,510 A | 10/1999 | Fugoso et al. |
| 5,980,486 A | 11/1999 | Enger |
| 6,042,578 A | 3/2000 | Dinh et al. |
| 6,071,273 A | 6/2000 | Euteneuer et al. |
| 6,159,195 A | 12/2000 | Ha et al. |
| 6,190,358 B1 | 2/2001 | Fitzmaurice et al. |
| 6,193,686 B1 | 2/2001 | Estrada et al. |
| 6,199,262 B1 | 3/2001 | Martin |
| 6,270,465 B1 | 8/2001 | Keith et al. |
| 6,299,628 B1 | 10/2001 | Harrison et al. |
| 6,338,725 B1 | 1/2002 | Hermann et al. |
| 6,398,773 B1 | 6/2002 | Bagaoisan et al. |
| 6,409,863 B1 | 6/2002 | Williams et al. |
| 6,443,912 B1 | 9/2002 | Mazzola et al. |
| 6,475,195 B1 | 11/2002 | Voda |
| 6,488,655 B1 | 12/2002 | Wantink et al. |
| 6,503,223 B1 | 1/2003 | Sekido et al. |
| 6,503,353 B1 | 1/2003 | Peterson et al. |
| 6,548,010 B1 | 4/2003 | Stivland et al. |
| 6,575,958 B1 | 6/2003 | Happ et al. |
| 6,591,472 B1 | 7/2003 | Noone et al. |
| 6,595,952 B2 | 7/2003 | Forsberg |
| 6,610,068 B1 | 8/2003 | Yang |
| 6,620,149 B1 | 9/2003 | Lenz et al. |
| 6,635,029 B1 | 10/2003 | Venturelli |
| 6,638,268 B2 | 10/2003 | Niazi |
| 6,648,874 B2 | 11/2003 | Parisi et al. |
| 6,689,144 B2 | 2/2004 | Gerberding |
| 6,706,018 B2 | 3/2004 | Westlund et al. |
| 6,733,487 B2 | 5/2004 | Keith et al. |
| 6,755,812 B2 | 6/2004 | Peterson et al. |
| 6,860,876 B2 | 3/2005 | Chen |
| 6,997,908 B2 | 2/2006 | Carrillo, Jr. et al. |
| 7,169,162 B2 | 1/2007 | Garakani |
| 7,232,452 B2 | 6/2007 | Adams et al. |
| 7,294,124 B2 | 11/2007 | Eidenschink |
| 7,374,560 B2 | 5/2008 | Ressemann et al. |
| 7,422,579 B2 | 9/2008 | Wahr et al. |
| 7,544,201 B2 | 6/2009 | Pepper |
| 7,604,612 B2 | 10/2009 | Ressemann et al. |
| 7,697,996 B2 | 4/2010 | Manning et al. |
| 7,717,899 B2 | 5/2010 | Bowe et al. |
| 7,736,355 B2 | 6/2010 | Itou et al. |
| 7,762,984 B2 | 7/2010 | Kumoyama et al. |
| 7,763,012 B2 | 7/2010 | Petrick et al. |
| 7,959,603 B2 | 6/2011 | Wahr et al. |
| 8,048,032 B2 | 11/2011 | Root et al. |
| 8,142,413 B2 | 3/2012 | Root et al. |
| 8,292,850 B2 | 10/2012 | Root et al. |
| 8,814,890 B2 | 8/2014 | Miyata et al. |
| RE45,380 E | 2/2015 | Root et al. |
| 8,996,095 B2 | 3/2015 | Anderson et al. |
| 9,144,662 B2 | 9/2015 | Caprio et al. |
| RE45,760 E | 10/2015 | Root et al. |
| RE45,776 E | 10/2015 | Root et al. |
| 9,352,123 B2 | 5/2016 | Zhou et al. |
| RE46,116 E | 8/2016 | Root et al. |
| 9,486,611 B2 | 11/2016 | Petersen et al. |
| 10,173,029 B2 | 1/2019 | Webster et al. |
| RE47,379 E | 5/2019 | Root et al. |
| 10,751,514 B2 | 8/2020 | Brenizer et al. |
| 2001/0016712 A1 | 8/2001 | Hamilton |
| 2002/0165598 A1 | 11/2002 | Wahr et al. |
| 2003/0195546 A1 | 10/2003 | Solar et al. |
| 2003/0233117 A1 | 12/2003 | Adams et al. |
| 2004/0010280 A1 | 1/2004 | Adams et al. |
| 2004/0127927 A1 | 7/2004 | Adams |
| 2004/0236215 A1 | 11/2004 | Mihara et al. |
| 2005/0004523 A1 | 1/2005 | Osborne et al. |
| 2005/0015073 A1 | 1/2005 | Kataishi et al. |
| 2005/0182437 A1 | 8/2005 | Bonnette et al. |
| 2006/0247661 A1 | 11/2006 | Richards et al. |
| 2007/0260219 A1 | 11/2007 | Root et al. |

(56) References Cited

U.S. PATENT DOCUMENTS

| | | |
|---|---|---|
| 2008/0082045 A1 | 4/2008 | Goldfarb et al. |
| 2008/0243171 A1 | 10/2008 | Ressemann et al. |
| 2009/0005755 A1 | 1/2009 | Keith et al. |
| 2009/0264865 A1 | 10/2009 | Kawai |
| 2013/0072904 A1 | 3/2013 | Musbach et al. |
| 2013/0116701 A1 | 5/2013 | Wang et al. |
| 2013/0197483 A1 | 8/2013 | Anderson et al. |
| 2013/0289697 A1 | 10/2013 | Baker et al. |
| 2014/0018773 A1 | 1/2014 | Wang et al. |
| 2014/0025043 A1 | 1/2014 | Wang et al. |
| 2014/0039461 A1 | 2/2014 | Anderson et al. |
| 2014/0081243 A1 | 3/2014 | Zhou et al. |
| 2014/0142506 A1 | 5/2014 | Prindle et al. |
| 2014/0259544 A1 | 9/2014 | Sigmon, Jr. |
| 2014/0276618 A1 | 9/2014 | Di Caprio et al. |
| 2015/0051633 A1 | 2/2015 | Sina |
| 2015/0151090 A1 | 6/2015 | Sutton et al. |
| 2016/0346515 A1 | 12/2016 | Buller et al. |
| 2017/0042571 A1 | 2/2017 | Levi |
| 2017/0296783 A1 | 10/2017 | Connolly et al. |
| 2018/0161547 A1* | 6/2018 | Brenizer ............ A61M 25/0113 |
| 2019/0247619 A1 | 8/2019 | Brenizer et al. |
| 2021/0008343 A1 | 1/2021 | Brenizer et al. |
| 2021/0008355 A1 | 1/2021 | Peterson et al. |
| 2022/0313950 A1 | 10/2022 | Brenizer et al. |

FOREIGN PATENT DOCUMENTS

| | | |
|---|---|---|
| EP | 0313558 B1 | 1/1991 |
| EP | 0380873 B1 | 5/1994 |
| EP | 0365993 B1 | 12/1994 |
| EP | 0881921 A1 | 12/1998 |
| EP | 1084728 A1 | 3/2001 |
| EP | 0992260 B1 | 9/2007 |
| EP | 3253437 A1 | 12/2017 |
| EP | 2968853 B1 | 2/2020 |
| JP | 168052 | 5/1989 |
| JP | 2004275435 A | 10/2004 |
| WO | 1984003633 A1 | 9/1984 |
| WO | 1997037713 A1 | 10/1997 |
| WO | 2000024451 A9 | 11/2000 |
| WO | 2016191415 A1 | 12/2016 |
| WO | 2017019900 A1 | 2/2017 |

OTHER PUBLICATIONS

Extended European Search Report dated Sep. 2, 2022, in European Patent Application No. 19889843.9.

Bertrand, Michel E. "The Evolution of Cardiac Catheterization and Interventional Cardiology," European Society of Cardiology, 2006, 10 pages.

Bonzel, T. et al. "The Sliding Rail System (Monorail): Description of a New Technique for Intravascular Instrumentation and its Application to Coronary Angioplasty," Z. Kardiol. 76, Supp. 6 (1987), pp. 119-122.

Iqbal et al. "Coronary stents: historical development, current status and future directions," British Medical Bulletin, 2013, 106: 193-211.

PCT International Search Report and Written Opinion dated Jan. 10, 2020 in PCT Application No. PCT/US2019/058783.

Takahashi, Saeko. "New Method to Increase a Backup Support of a 6 French Guiding Coronary Catheter," Catheterization and Cardiovascular Interventions 63:452-456 (2004), 5 pages, published online in Wiley InterScience (www.interscience.wiley.com).

Topol, Eric J. "Textbook of Interventional Cardiology," Saunders Elsevier, 5th Edition, 2008, p. 277-280.

Tully, Shawn. "Blood Feud This little piece of metal is worth $4.5 billion this year, generates more profits than a blockbuster drug, and has sparked one of the weirdest corporate battles ever. It could also save your life." CNN Money, May 31, 2004, 5 pages. Retrieved Jan. 14, 2019 on the Internet.

Vascular Solutions, Inc. "GuideLiner V3 catheter: Guide Extension Catheter with Half-Pipe Technology" [Brochure], Dec. 2013, Minneapolis, MN.

* cited by examiner

GUIDE EXTENSION CATHETER

CLAIM OF PRIORITY

This application is a national stage application under 35 U.S.C. § 371 of PCT application no. PCT/US2019/058783, filed Oct. 30, 2019, which claims priority to U.S. provisional patent application No. 62/771,658, entitled "GUIDE EXTENSION CATHETER" and filed on Nov. 27, 2018, both of which are herein incorporated by reference in their entirety.

TECHNICAL FIELD

The subject matter of this patent document relates to the field of medical devices. More particularly, but not by way of limitation, the subject matter relates to guide extension catheters for use with guide catheters.

BACKGROUND

Interventional cardiology procedures often involve inserting treatment guidewires or other instruments through catheters into coronary arteries that branch off from the aorta. In coronary artery disease, the coronary artery may be narrowed or occluded by atherosclerotic plaques or other lesions. These lesions may totally obstruct the lumen of the artery or may dramatically narrow the lumen of the artery. Narrowing is referred to as stenosis. In order to diagnose and treat obstructive coronary artery disease, it is commonly necessary to pass a treatment guidewire or other instruments through and beyond the occlusion or stenosis of the coronary artery.

To treat a stenosis, a guide catheter can be inserted through the aorta and into the ostium of the coronary artery. This is sometimes accomplished with the aid of an introducer guidewire. The guide catheter is typically seated adjacent the opening or ostium of the artery to be treated and a treatment guidewire or other instrument is passed through the lumen of the guide catheter and inserted into the artery beyond the occlusion or stenosis. Crossing tough lesions or tortuous anatomy can create enough backward force to dislodge the guide catheter from its position adjacent the ostium of the artery being treated. This can make it difficult or impossible for the interventional cardiologist to treat certain forms of coronary artery disease.

A coaxial guide catheter can be used in conjunction with a standard guide catheter to provide additional backup support. The coaxial guide catheter can be passed through the standard guide catheter until its distal end extends beyond the distal end of the standard guide catheter, thereby positioning the distal end of the coaxial guide catheter within the branch artery harboring the stenosis. Coaxial guide catheters may thus be referred to as guide extension catheters.

Overview

The present inventors recognize that there is a need to provide guide extension catheters that are compatible with guide catheters for performing interventional procedures in challenging anatomy, e.g., narrow blood vessels harboring robust occlusions. The present inventors also recognize that there is a need to provide increased back-up support to interventional devices and guide catheters during interventional procedures. A guide extension catheter that includes guide extension tubing can be used in conjunction with a guide catheter to access discrete regions of coronary vasculature and to facilitate accurate placement of interventional devices without guide catheter backout from a vessel ostium or branch of interest.

The present inventors further recognize that holding guide extension catheters in place during an operation can be difficult, especially when multiple interventional devices are employed simultaneously. Movement of the guide extension catheter may result in one or more instruments becoming dislodged from the treatment site, which may be difficult to re-access. Accordingly, new devices or techniques capable of securing guide extension catheters in place during use are needed.

Guide extension catheters and related methods are disclosed in this patent document. A guide extension catheter can comprise an elongate tube member (also referred to as guide extension tubing) and a push member (also referred to as a substantially rigid portion). The push member, which may not have a lumen large enough to allow passage of interventional cardiology devices, can be eccentrically coupled to the tube member for slidably positioning the tube member within and partially beyond a distal end of a guide catheter and into a vessel ostium of interest. A proximal end or portion of the push member can be coupled with a proximal manipulation member configured to secure the guide extension catheter in place during use.

These and other embodiments and features of the present guide extension catheters and related methods will be set forth, at least in part, in the following Detailed Description. This Overview is intended to provide non-limiting embodiments of the present subject matter; it is not intended to provide an exclusive or exhaustive explanation of the disclosed embodiments. The Detailed Description below is included to provide further information about the present guide extension catheters and methods.

BRIEF DESCRIPTION OF THE DRAWINGS

In the drawings, like numerals can be used to describe similar features and components throughout the several views. The drawings illustrate generally, by way of example, but not by way of limitation, various embodiments discussed in this patent document.

The drawings are not necessarily to scale. Certain features and components may be shown exaggerated in scale or in schematic form, and some details may not be shown in the interest of clarity and conciseness.

DETAILED DESCRIPTION

This patent document discloses guide extension catheters to be placed within guide catheters for providing support and guidance in a vessel when percutaneously advancing interventional devices, such as guidewires, balloon catheters, stents or stent catheters. A guide extension catheter is configured to be passed through a continuous lumen of a guide catheter so that its distal end portion can be extended past a distal end of the guide catheter and into the desired vessel while its intermediate portions remain within the guide catheter, for example as described in U.S. Pat. Nos. 8,048,032, 8,142,413, RE45,760, RE45,776, and RE46,116, which are incorporated by reference in their entireties herein. The guide extension catheter improves the ability of the guide catheter to remain seated in the desired vessel's ostium or branch during an interventional procedure. A manipulation member attached to a proximal end or portion of the guide extension catheter can secure the guide extension catheter during use, thereby simplifying manipulation of the guide extension catheter and minimizing device entanglement.

It is believed that the present guide extension catheters will find great utility by interventional cardiologists performing percutaneous transluminal coronary interventions. Although the remainder of this patent document generally discusses and illustrates such uses, it should be understood that the guide extension catheters can also be used for treating other non-coronary diseased vessels or other hollow structures (e.g., biliary tract, ureter, etc.) throughout a patient's body where interventional devices are or can be employed.

Figure 1:
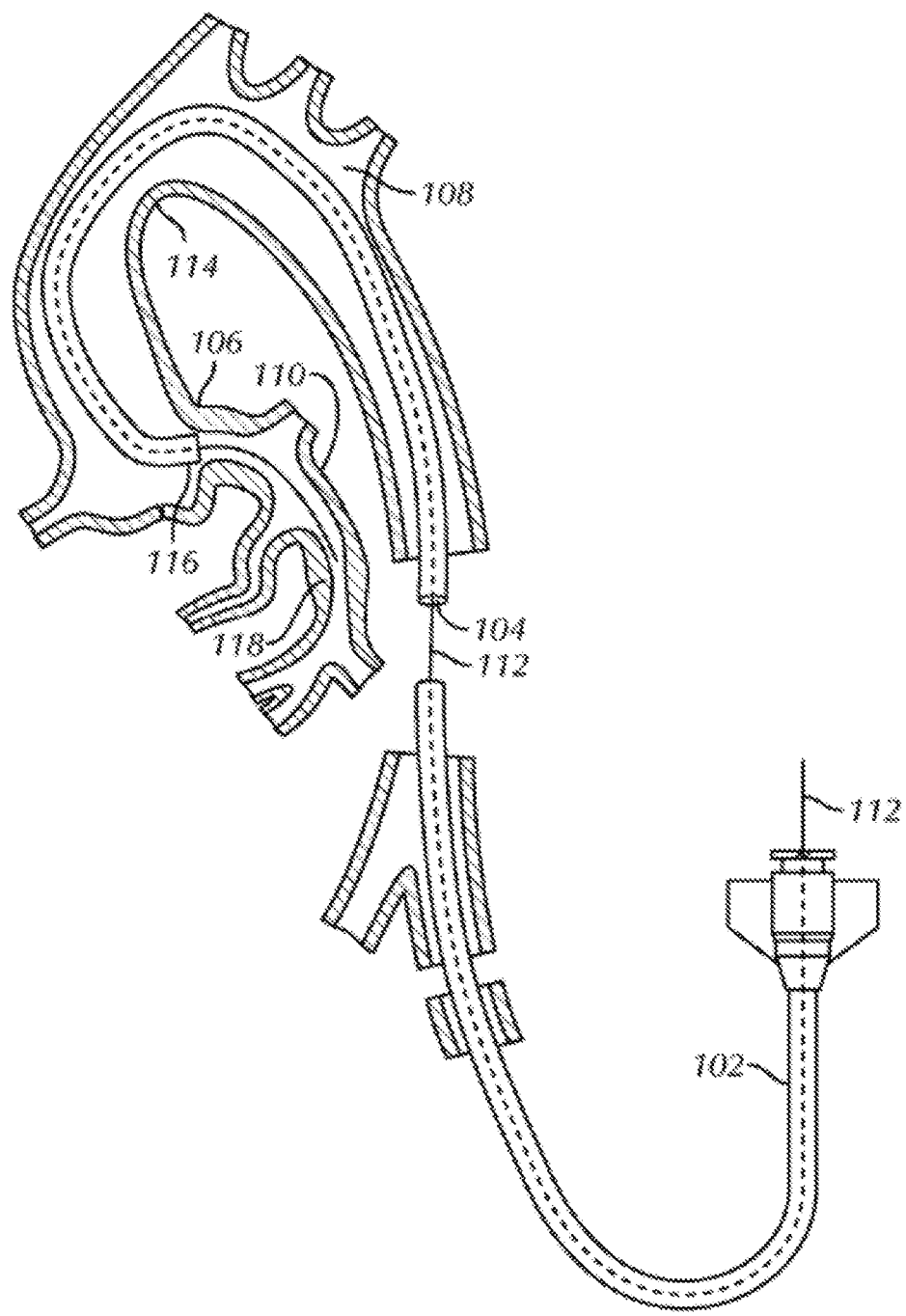
FIG. 1 illustrates a plan view of a guide catheter advanced through an aorta to an ostium of a coronary vessel.

Minimally invasive cardiac interventions are utilized throughout the world and often include the use of a treatment guidewire 112 and a guide catheter 102, as illustrated in FIG. 1. The guidewire 112 can comprise an elongate, small-diameter member designed to navigate vessels to reach a diseased site or vessel segment of interest. Guidewires can come in various configurations, including solid steel or nitinol core wires and/or solid core wire wrapped in a smaller wire coil or braid, for example. The guide catheter 102 can comprise an elongate tube member defining a main or continuous lumen 104 along its length. The guide catheter 102 can be formed of polyurethane, for example, and can be shaped to facilitate its advancement to a coronary ostium 106 (or other region of interest within a patient's body). Any sized guide catheter 102, such as a 6F, 7F, 8F guide catheter, where F is an abbreviation for the French catheter scale (a unit to measure catheter diameter (1F=⅓ mm)), can be inserted at a femoral or radial artery and advanced through an aorta 108 to a position adjacent to the ostium 106 of a coronary artery 110.

In a typical procedure, an insertion guidewire or the treatment guidewire 112 and guide catheter 102 can be advanced through the arch 114 of the aorta 108 to the ostium 106. The guidewire 112 may then be advanced beyond the ostium 106 and into the coronary artery 110. The diameter and rigidity of the guide catheter's distal end 116, however, may not permit the device to be safely advanced beyond the ostium 106 and into the coronary artery 110.

Maintaining the position of the guide catheter's distal end 116 at the ostium 106 can facilitate the guidewire 112 or other interventional device successfully reaching the diseased site (e.g., a stenotic lesion 118) through its further distal advancement. With the guide catheter 102 in position, force can be applied to the guidewire's proximal end to push the guidewire 112 to and beyond the lesion 118, and a treating catheter (optionally including a balloon or stent) can be passed over the guidewire 112 to treat the site. The application of force to the guidewire 112 or the treating catheter can sometimes cause the guide catheter 102 to dislodge from the ostium 106 of the coronary artery 110, and, in such instances, the guidewire or treating catheter must be further distally advanced independently of the guide catheter's alignment and support to reach the lesion 118. This can occur in the case of a tough stenotic lesion 118 or tortuous anatomy, where it is often difficult to pass the guidewire 112 or the treating catheter to and beyond the lesion. A heart's intrinsic beat can also cause the guide catheter's distal end 116 to lose its positioning or otherwise be shifted so that it no longer is positioned to align and support the guidewire 112 or the treating catheter into the portion of the coronary artery 110 including the lesion 118.

Figure 2:
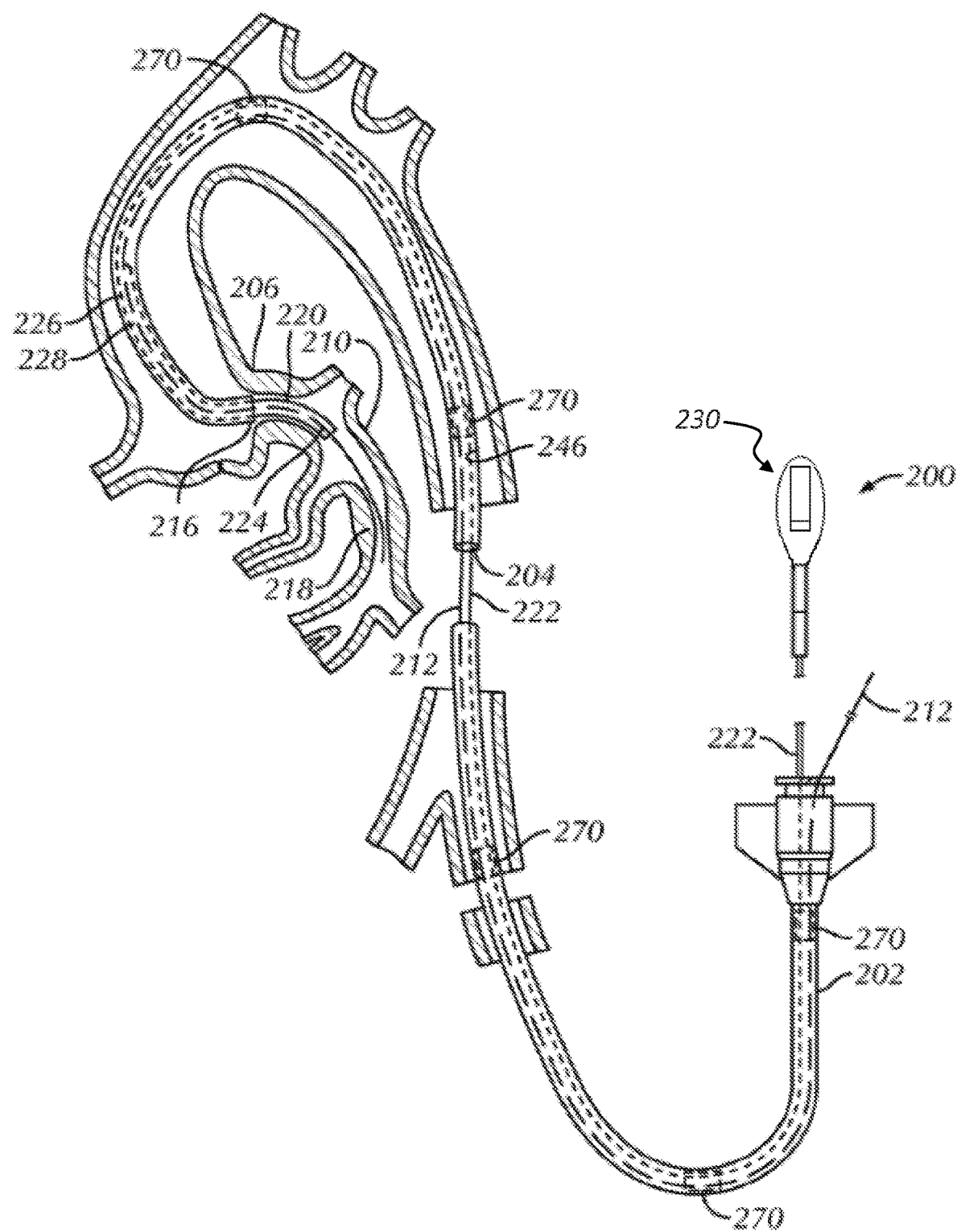
FIG. 2 illustrates a plan view of a guide extension catheter, as constructed in accordance with at least one embodiment, used in conjunction with a guide catheter for the delivery of an interventional device into an occluded vessel for treatment.

As illustrated in FIG. 2, the present guide extension catheter 200 can improve access to a coronary artery 210 and a stenotic lesion 218. The guide extension catheter 200 can include a relatively flexible elongate tube member 220 and a push member 222 having a collective length that is greater than a length of a guide catheter 202 (e.g., 130 cm-175 cm, or greater). An outer diameter of the tube member 220 can be sized to permit insertion of its distal end portion 224 into a coronary artery or its branches containing the lesion 218, thereby providing alignment and support for an interventional device (e.g., a treating catheter) beyond the distal end 216 of the guide catheter 202 to the lesion and beyond. The extension of the tube member 220 into the smaller-sized artery or branch also serves to maintain the position of the guide catheter 202 at an artery's ostium 206 during operation.

The operating physician can advance the distal end portion 224 of the tube member 220 over a guidewire 212 and through and beyond the guide catheter's distal end 216 into the coronary artery 210. A proximal end portion 226 of the tube member 220 can remain within the guide catheter 202. The physician can then deliver the treating catheter over the guidewire 212, through a main lumen 204 of the guide catheter 202, and through a lumen 228 of the tube member 220 until the working portion of the treating catheter is located beyond the distal end portion 224 of the tube member. The operating physician can then treat the lesion 218 using standard techniques with added back-up support on the guide catheter 202, thereby providing an extra ability to push and advance the treating catheter.

In general, the lumen 228, and hence the tube member 220, can be sized and shaped to pass one or more interventional devices such as the guidewire and the treating catheter therethrough. The cross-sectional shape of the lumen 228 can be similar to the cross-sectional shape of the guide catheter's main lumen 204. For instance, in some examples, the cross-sectional shape of the lumen 228 can be substantially uniform along its length. In other examples, the cross-sectional diameter may vary along the length of the tube member 220. According to embodiments of such examples, the distal end portion 224 of the tube member 220 may be more narrow, e.g., tapered, relative to the proximal end portion 226, for instance. In addition or alternatively, the proximal and distal portions of the tube member 220 can be separated by one or more tapered portions. The length of each differently-sized portion of the tube member 220 in such embodiments can also vary, and in some examples, the distal portion 224 of the tube member can be the longest. In examples that include differently sized proximal and distal portions, the difference in diameter between the proximal portion 226 and the distal portion 224 of the tube member may be from about 1F to about 4F, or anywhere in between.

The outer diameter of the tube member 220 can assume maximum cross-sectional dimensions that allow the tube member 220 to coaxially slide into and through the guide catheter 202. In other embodiments, the outer cross-sectional dimensions of the tube member 220 can be less than the allowable maximum. For example, in an 8F guide catheter, the tube member 220 can have a 7F, 6F, 5F, 4F or lesser diameter. In some embodiments, a diameter of the lumen 228 of the tube member 220 is not more than about one French size smaller than a diameter of the lumen 204 of the guide catheter 202. In one embodiment, the guide extension catheter 200 can be made in at least three sizes corresponding to the internal capacity of 8F, 7F, and 6F guide catheters that are commonly used in interventional cardiology procedures. The difference in size between the outer diameter of the tube member 220 and the inner diameter of the guide catheter may vary. For instance, the gap in cross-sectional diameter between the inner diameter of the guide catheter and the outer diameter of the tube member 220 may be less than and/or about 0.001 in., 0.002 in., 0.003 in., 0.004 in., or 0.005 in., or any distance therebetween. In specific embodiments, the cross-sectional diameter gap may range from about 0.002 to 0.003 in., or about 0.002 to 0.0035 in. The diameter gap may be substantially continuous along a substantial portion of the length or a majority of the length of the tube member 220 in some examples, or the gap may increase along one or more distal portions of the tube member 220. In various embodiments, a tube member 220 with any diameter may be used. The length of the tube member 220 can be substantially less than the length of the guide catheter 202; however, the tube member 220 can be designed with any length according to a desired application, such as about 6 to about 45 cm, about 10 to about 35 cm, about 14 to about 25 cm, or about 18 to about 20 cm.

The push member 222 can be attached to the proximal end portion 226 of the tube member 220 and can extend proximally from this attachment to a manipulation member 230 (also referred to as a handle or coupling member) accessible to an operating physician outside of a patient's body. The manipulation member 230 and the push member 222 can allow the physician to position the tube member 220 between a first position, entirely within the guide catheter 202, and the illustrated second position, in which the tube member's distal end 224 extends beyond that of the guide catheter 202 and into the coronary artery 210. The push member 222 can comprise a substantially rigid portion that is rigid enough to allow the guide extension catheter 200 to be inserted through the guide catheter 202 upon receiving a pushing force from a physician via the manipulation member 230. The push member 222 can be more rigid along its longitudinal axis than the tube member 220, and may generally define a rail structure without a lumen through which interventional cardiology devices are insertable. In some examples, the push member 222 can have a maximal cross-sectional dimension at a proximal portion that is smaller than the cross-sectional outer diameter of the tubular flexible portion.

In some embodiments, the push member 222 can include one or more tubular or elongate structures, such as tubular bands 270, along its length to urge the member to one side of the guide catheter's inner wall surface 246, for example as described in U.S. patent application Ser. No. 15/581,176, which is incorporated by reference in its entirety herein. Once the tube member's distal end 224 reaches a targeted position, the manipulation member 230 can be secured externally, such that the guide extension catheter 200 remains stationary. In some examples, the manipulation member 230 may be secured by coupling it, e.g., clipping or clamping, to an external object, such as the patient's gown or a portion of operating equipment. In addition or alternatively, the manipulation member 230 may be secured by its own weight, such that it can be simply set on a flat, or relatively flat, surface to secure the guide extension catheter 200 in place without coupling the manipulation member 230 to an external object. In some examples, the manipulation member 230 can be formed of one or more polycarbonate materials.

Figure 3:
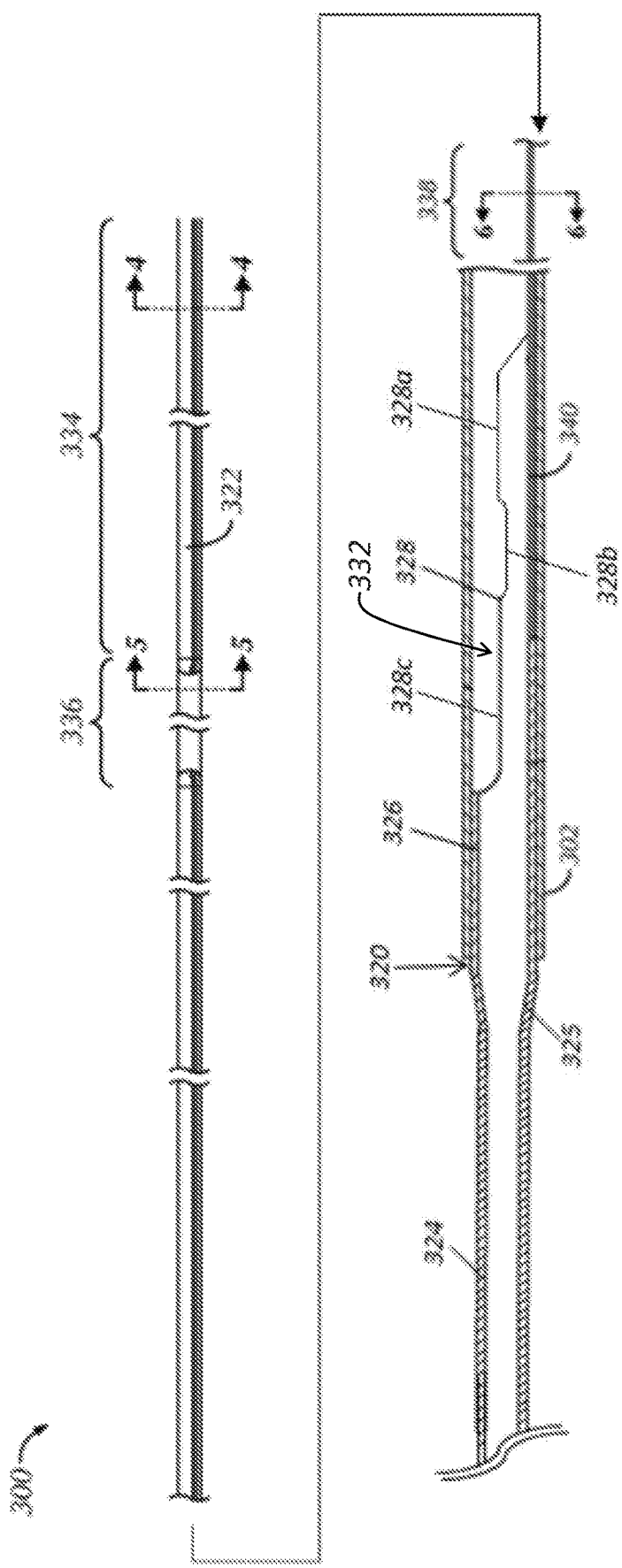
FIG. 3 illustrates a side view of a guide extension catheter, as constructed in accordance with at least one embodiment, partially within a sectioned guide catheter.

FIG. 3 illustrates a side view of an example guide extension catheter 300 partially positioned within a guide catheter 302. This side view illustrates in greater detail the components of the guide extension catheter 300 according to one embodiment, including a relatively flexible elongate tube member 320 and a push member 322. The push member 322 can be rigid enough to urge the tube member 320 through the vasculature in response to receiving an axial force applied at a proximal end thereof, e.g., by a physician. The stiffness of the push member 322 may be uniform, or substantially uniform, along its length. In certain examples, the push member 322 can include a plurality of segments or portions having different stiffness and flexibility profiles to provide the guide extension catheter 300 with a desired combination of pushing force and vessel placement capabilities. In one embodiment of such examples, the push member 322 can include three segments 334, 336, 338 having different stiffness and flexibility profiles: relative high stiffness and low flexibility at a proximal end portion 334 of the push member, relative medium stiffness and flexibility in an intermediate portion 336 of the push member, and relative low stiffness and high flexibility at a distal end portion 338 of the push member. In some embodiments, the length of the first segment 334 can constitute between 50% and 90% of the entire length of the guide extension catheter 300, the length of the third segment 338 can constitute between 2% and 10% of the catheter's length, and the remaining length can be attributed to the second segment 336. More or less segments of differing stiffness and flexibility profiles can also be used and accomplished through variation of one or more materials, geometric shapes or geometrical sizes of the push member 322. The length of each segment may also vary.

In some embodiments, the push member 322 can be an elongated solid wire of constant or varying dimensions and can be made of a polymeric or metallic material, such as high tensile stainless steel (e.g., 304V, 304L or 316LV), mild steel, nickel-titanium allows, nickel-chromium-molybdenum alloys, nickel-copper alloys, nickel-tungsten alloys or tungsten alloys. The push member 322 can be coated with a hydrophilic, silicone or other friction-reducing material.

In some examples, the tube member 320 can be formed from an inner polymer layer, an outer polymer layer, and/or a reinforcement member (e.g., braid or coil) disposed between or adjacent to the polymer layers. According to such examples, the inner polymer layer can be composed of, or coated with, silicone, polytetrafluoroethylene (PTFE) or another lubricious material to provide a slippery surface for received interventional devices. The outer polymer layer can include one or more flexible materials, such as polyurethane, polyethylene or polyolefin of sequentially diminishing durometers along the tube member's length, and it can be coated with a friction-reducing material (e.g., a hydrophilic material) to facilitate insertion and trackability through vasculature and a guide catheter. The reinforcing braid or coil, in embodiments featuring a braid or coil, can be formed of stainless steel or a platinum alloy, for example, and can extend between the polymer layers along at least a portion of the tube member's length.

Figure 9A:
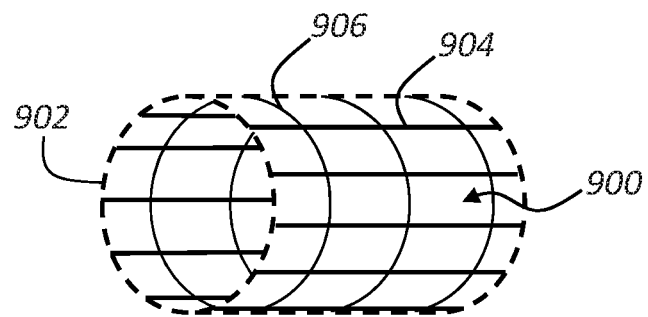
FIG. 9A illustrates a perspective view of a reinforcement member included in a guide extension catheter in accordance with at least one embodiment.
Figure 9B:
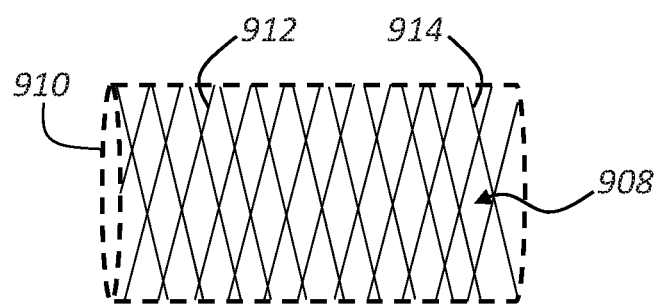
FIG. 9B illustrates a perspective view of another reinforcement member included in a guide extension catheter in accordance with at least one embodiment.

The optional reinforcement member disposed between the polymer layers of some elongate tube members 320 can be configured in multiple ways. For instance, the reinforcement member may lack a braid, coil or other distinct reinforcing structure, and may instead comprise one or more materials having greater stiffness than the remaining portions of the tube member 320. In addition or alternatively, embodiments of the reinforcement member can include different reinforcing structures, e.g., a rigid sleeve, elongate member, and/or bars or strips of rigid or semi-rigid material, as shown in FIGS. 9A and 9B. Additional components and/or materials configured to increase the rigidity of a portion of the tube member 320 are also contemplated. At least in part because the components of the reinforcement member may vary, methods of assembling the reinforcement member may also vary. For example, if the reinforcement member disposed between the polymer layers of the elongate member 320 includes a coil, various types of coils may be used, and in some examples, each coil can be coupled with other components of the tube member 320 in a distinct manner, which may depend on whether the cross-sectional diameter of the tube member is uniform or varied. In embodiments, if the size of the coil matches the smaller distal portion 324 of the tube member 320, the coil can be first loaded over the distal portion 324. If the size of the coil is larger, such that it approximately matches the larger diameter of the proximal portion 326, the coil can be first loaded onto the proximal portion 326.

A proximal end portion 326 of the tube member 320 can be eccentrically coupled to a distal end portion 340 of the push member 322 at its periphery or circumference and can provide a smooth transition between the members in some examples. The arrangement or configuration of this coupling can vary. For example, the tube member 320 can include a side opening formed at a proximal end of its peripheral wall. The configuration of the side opening may also vary. For example, the side opening may be sloped or slanted such that the transition between the push member 322 and the full circumferential portion of the tube member 320 is relatively gradual. In some examples, the push member 322 can be disposed within the opening. Inserting the push member 322 into the opening can result in a mechanical coupling between the members and additional or alternative bonds (e.g., adhesive bonds, thermal bonds, welds, brazes, etc.) can be utilized. The distal end portion 340 of the push member 322 can be flattened in some embodiments to provide a larger surface area to secure to the tube member 320. In addition or alternatively, coupling mechanisms facilitated by a third component 332 (e.g., a metal or polymer skived (slanted) collar or concave track) bonded between or integrated with the proximal end portion 326 of the tube member 320 or the distal end portion 340 of the push member 322 are also contemplated. Metallic or polymeric structures forming the third component 332 can become less stiff and more flexible in a proximal-to-distal direction, for instance, to provide a gradual flexibility transition between the more rigid push member 322 and the more flexible tube member 320.

In embodiments featuring a concave track 328, such as the example shown in FIG. 3, the degree of enclosure defined by the concave track 328 can vary along its length. In one embodiment, a first segment 328a of the concave track 328 can define an approximately 200° enclosure, a second segment 328b of the concave track can define an approximately 170° enclosure, and a third segment 328c, closer to the tube member 320, can define an approximately 200° enclosure, which transitions to 360° just before reaching the most proximal end of the tube member's proximal portion 326. Accordingly, the concave track 328 may transition, proximally to distally, from more enclosed to less enclosed, and back to more enclosed before reaching the proximal end portion 326 of the tube member 320. The specific degree of enclosure defined by each portion of the concave track 328 may vary, along with the number of distinct portions constituting the concave track 328. For example, the degree of enclosure defined by each portion may be increased or decreased by up to 5°, 10°, 15°, 20°, 25°, 30°, 40°, 50°, 60°, or more. In operation, the intermediary valley of the concave track 328, i.e., the second segment 328b, along with the embedded push member 322, may be urged to one side of the guide catheter's inner wall surface such that the track 328 and push member 322 may be concentrically aligned within guide catheter 302, thereby providing a clear path through the guide catheter and into the tube member 320 for a guidewire and a treating catheter. This clear path can eliminate twisting and prevent a guidewire, e.g., guidewire 212, from becoming entangled with, e.g., wrapped around, the push member 322 during use of the guide extension catheter 300. Alleviation of twisting may be especially apparent in operations requiring multiple, simultaneously inserted guidewires.

In some embodiments, the concave track 328 can define a partially cylindrical opening, e.g., resembling a half-pipe, and having a length of about 1 cm to about 4 cm, 8 cm, 12 cm, 16 cm, 18 cm, 20 cm, 22 cm, 24 cm, 26 cm, or more, or any length therebetween. In one example, the concave track 328 may be about 17 cm long. In various embodiments, the length of each discernible portion 328a, 328b, 328c of the concave track 328 may range from about 1 cm, 2 cm, 4 cm, 6 cm, 8 cm, 10 cm, or 12 cm. The length of each portion 328a, 328b, 328c may be the same or different. In some examples, the concave track 328 may include less than three distinct portions. For example, the concave track 328 may define an elongated tapered portion. The concave track 328 can be accessible from a longitudinal side defined transverse to a longitudinal axis of the tube member 320 and can provide a larger area to receive an interventional device into the tube member than an area associated with an opening oriented perpendicular to the longitudinal axis of the tube member 320. Optionally, the concave track 328 can be sized larger than the proximal end portion 326 of the tube member 320 to more effectively align and funnel a treating catheter across the coupling transition and into the tube member 320. This larger size of the concave track 328 can be accomplished by incorporating a nickel-titanium alloy, for example, which can expand post-implant to a size of the guide catheter's inner wall surface.

Markers on the push member 322 or the tube member 320 can allow an operating physician to identify positioning of the guide extension catheter's components relative to patient anatomy, the guide catheter 302, and any interventional devices used during a procedure. For example, one or more depth markers can be printed on an outer surface of the push member 322 and can be positioned at predetermined lengths relative to a distal end of the tube member 320. One or more radiopaque marker bands can be positioned on the tube member 320. The marker bands can be composed of tungsten, platinum or an alloy thereof and can have a metallic band structure. Alternatively, for space conservation reasons, the marker bands can be formed by impregnating portions of the tube member 320 with a radiopaque filler material, such as barium sulfate, bismuth trioxide, bismuth carbonate, powdered tungsten, powdered tantalum or the like. A first marker band can be positioned slightly distal to a fully-round entrance of the tube member 320 and a second marker band can be positioned near the tube member's distal end, for example.

Methods of manufacturing the guide extension catheters described herein may involve stretching an inner PTFE lining of the elongate tube member 320. In embodiments featuring a tapered elongate tube member 320, the PTFE lining may require excess stretching relative to comparable, but non-tapered tube members, and the outer surface of the lining can be etched to maintain the desired polymer chemistry of the PTFE, thereby ensuring adhesion between the fluoropolymers of the lining and an outer polymer layer (e.g., PEBAX) wrapping.

Figure 4:
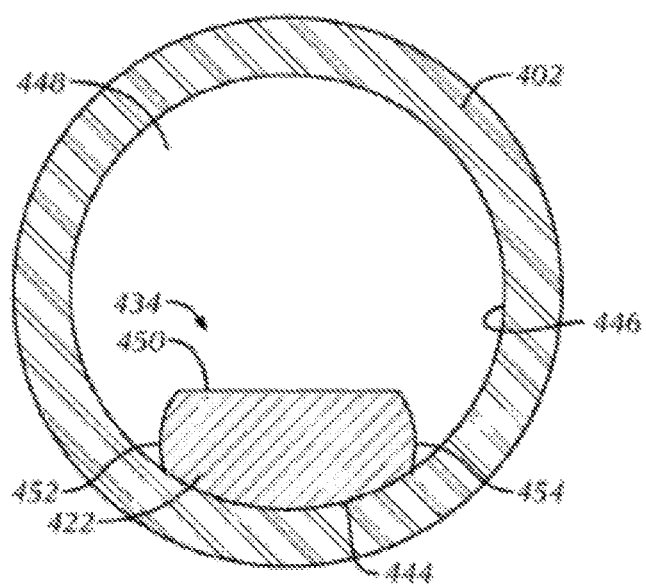
FIGS. 4-6 illustrate cross-sectional views along the length of a guide extension catheter, as constructed in accordance with at least one embodiment, within a guide catheter.

FIG. 4 illustrates a cross-sectional view of a proximal end portion 434 of an example push member 422, such as along line 4-4 of FIG. 3, within a guide catheter 402. The cross-sectional shape and dimensions of the push member 422 may vary. In the example shown, the cross-section can be defined by an arcuate first surface 444 configured to engage an inner wall surface 446 of the guide catheter 402. The arcuate or curved shape of the first surface 444 can follow the inner wall surface 446 of the guide catheter 402, providing smooth relative movements between the guide extension catheter and the guide catheter. The arcuate shape of the first surface 444 can also help to maximize axial or column strength of the push member 422 for force transfer from an operating physician to the rest of the guide extension catheter without reducing the effective delivery area 448 within the guide catheter 402 through which an interventional device can be advanced, for example as described in U.S. patent application Ser. No. 15/581,176, which is incorporated by reference in its entirety herein.

A second surface 450 of the proximal end portion's cross-section, which can be positioned opposite the first surface 444, can be flat, substantially flat, or curved.

The cross-section at the proximal end portion of the push member 422 can be further defined by third and fourth surfaces 452, 454, which may also be arcuate, that connect the first and second surfaces 444, 450.

The guide extension catheters disclosed herein can include one or more push members of various configurations. For instance, additional embodiments of the push member 422 may lack one or more features illustrated in FIG. 4. The push member 422 may not define, for example, an arcuate first surface 444 and/or an arcuate third or fourth surface 452, 454. Such embodiments may feature one or more substantially straight or concave surfaces of varying cross-sectional dimensions.

Figure 5:
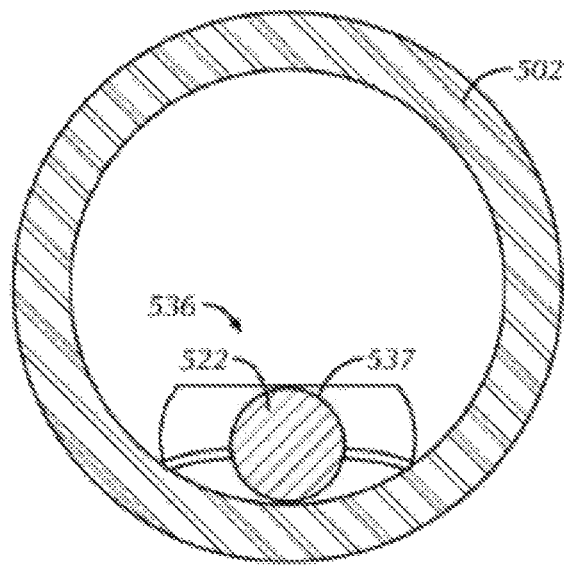

FIG. 5 illustrates a cross-sectional view of an intermediate portion 536 of an example push member 522, such as along line 5-5 of FIG. 3, within a guide catheter 502. As shown, the intermediate portion 536 can be circular or oval in cross-section and defined by a circumferential surface 537, which can reduce the tendency for a guidewire to become engaged with the push member 522 during use.

Alternatively, the intermediate portion 536 can be rectangular in cross-section and defined by first, second, third and fourth flat surfaces, or can be bread loaf in cross-section and defined by three arcuate surfaces and one flat surface like the proximal end portion. In these alternative embodiments, a distance change between center points of the first and second surfaces at the push member's proximal end portion (FIG. 4) to center points of the first and second surfaces at the push member's intermediate portion may be less than a distance change between center points of the third and fourth surfaces at the push member's proximal end portion to center points of the third and fourth surfaces at the push member's intermediate portion.

As yet another alternative, the intermediate portion 536 can have a cross-section defined by arcuate first and second surfaces. An arcuate first surface can have the same or substantially the same radius of curvature as the guide catheter's inner wall surface. An arcuate second surface can extend from a first end of the first surface to a second end of the first surface. Regardless of shape, the cross-section of the intermediate portion 536 of the push member can define an area less than an area of the cross-section of the proximal end portion (FIG. 4) of the push member 522 in some examples.

Figure 6:
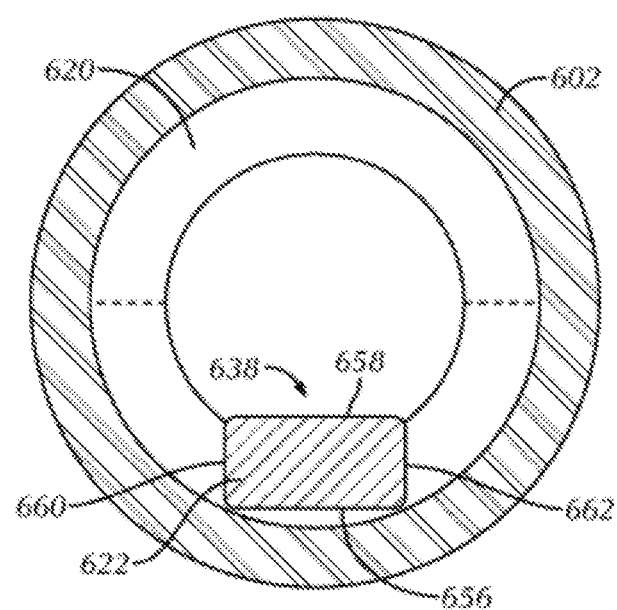

FIG. 6 illustrates a cross-sectional view of a distal end portion 638 of an example push member 622, such as along line 6-6 of FIG. 3, within a guide catheter 602. The distal end portion 638 can be rectangular in cross-section and defined by first, second, third and fourth surfaces 656, 658, 660, 662, which may be flat, substantially flat, or curved. The cross-section of the distal end portion 638 can define an area less than an area of the cross-section of the proximal end (FIG. 4) and intermediate (FIG. 5) portions of the push member 622 in some examples. The cross-section of the proximal end portion can gradually transition along the length of the push member 622 to the distal end portion 638, which can couple to a tube member 620. The distal end portion 638 can define a flattened rectangular cross-section in some examples, or alternatively can define a bread loaf cross-sectional shape defined by three arcuate surfaces and one flat or substantially flat surface. Additional cross-sectional shapes and dimensions of the distal end portion 638 are also contemplated, and the guide extension catheters disclosed herein are not limited to one or more configurations of the push member 622.

FIGS. 4-6 illustrate that the push member 422, 522, 622 of a guide extension catheter can be designed to be sufficiently small taking up relatively little space within the lumen of a guide catheter, while still being sufficiently sized and configured for exceptional pushability and kink resistance when advancing the extension catheter during an interventional procedure. Accordingly, use of the present guide extension catheters allows for an interventional device to be advanced through and beyond the guide catheter to reach a desired distal target location for intervention.

Figure 7:
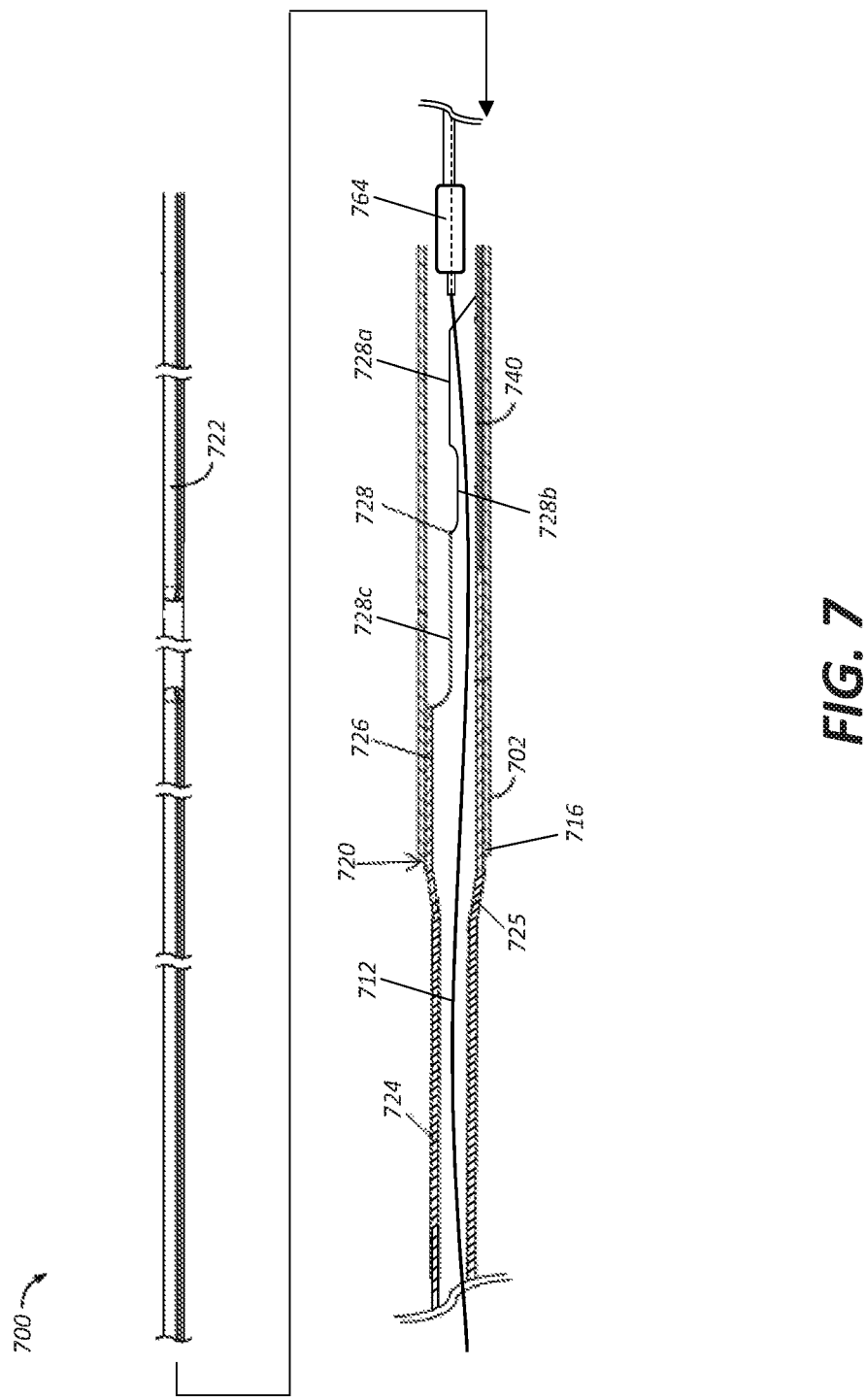
FIG. 7 illustrates a side view of a guide extension catheter, as constructed in accordance with at least one embodiment, and an interventional device partially within a sectioned guide catheter.

FIG. 7 illustrates a side view of an example guide extension catheter 700 positioned within a guide catheter 702 and used in conjunction with a guidewire 712 and a treating catheter 764. With the guidewire 712 and the guide catheter 702 positioned as desired, a tube member 720 of the guide extension catheter 700 can be backloaded from its narrow distal end portion 724 onto a proximal end of the guidewire 712 and advanced through a hemostasis valve coupled to the guide catheter 702. As shown, the tube member 720 of the guide extension catheter 700 can be advanced beyond a distal end 716 of the guide catheter 702 under fluoroscopy. When so arranged, portions of the tube member 720 can engage an ostium and extend within a portion of a coronary artery to help maintain the position of the guide catheter 702 as the treating catheter 764 is advanced. As further shown, embodiments of the guide extension catheter 700 can include a concave track 728, which may provide a variable degree of enclosure at portions 728a, 728b, and 728c to prevent or reduce twisting of the guidewire 712.

Figure 8C:
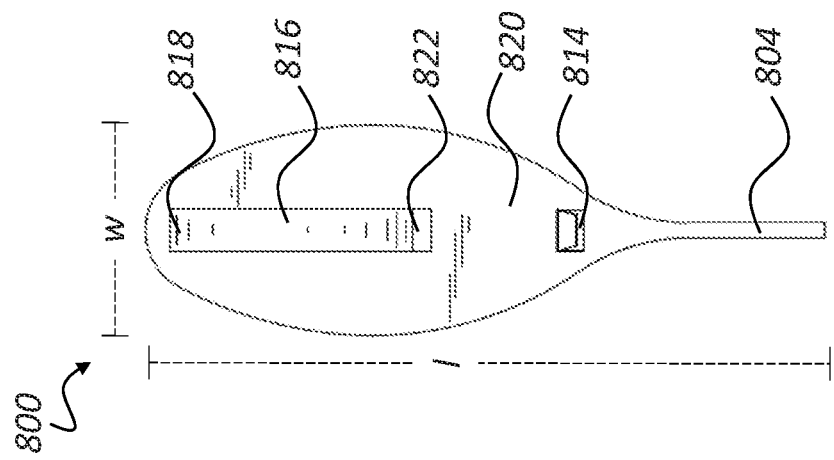
FIG. 8C illustrates a back view of the manipulation member of FIG. 8A.
Figure 8B:
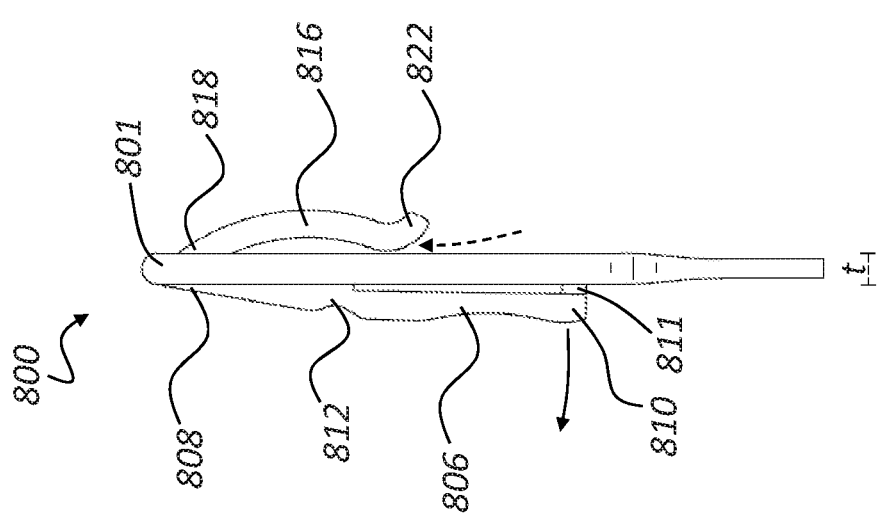
FIG. 8B illustrates a side view of the manipulation member of FIG. 8A.
Figure 8A:
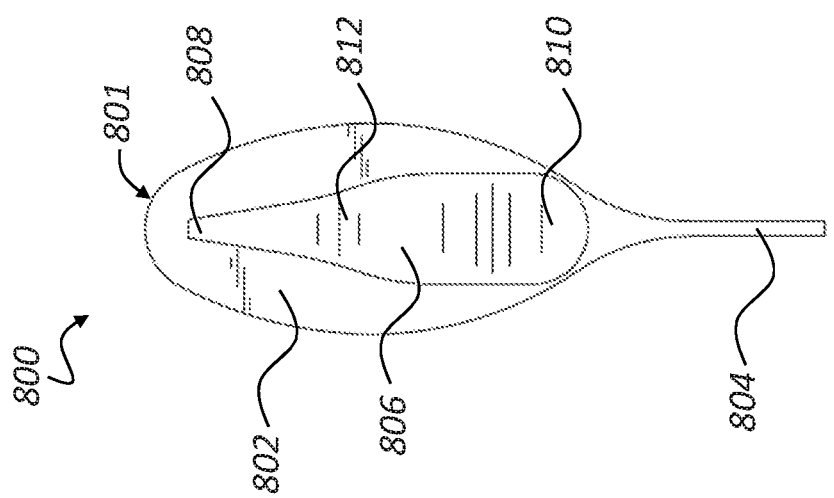
FIG. 8A illustrates a front view of a manipulation member, as constructed in accordance with at least one embodiment, included with a guide extension catheter.

FIGS. 8A-8C illustrate an example manipulation member 800 configured to secure the disclosed guide extension catheters in place during use. The manipulation member 800 can provide hands-free securing means, such that a user, e.g., physician or operating assistant, does not need to manually hold or grasp the manipulation member 800 in order to maintain the guide extension catheter in place during an operation. As shown, one embodiment of the manipulation member 800 can include a front surface 802, which may taper into a comparatively narrow attachment portion 804. The attachment portion 804 may be fixed, attached or otherwise coupled to a proximal end of a guide extension catheter, e.g., a proximal end of the push member. Protruding from the front surface 802 is a first coupling member 806, e.g., an optionally resilient tab or clip, which can be integrally formed with the front surface 802 at a first end 808 and reversibly coupled with the front surface 802 at a second end 810 in some examples. In additional or alternative embodiments, the first coupling member 806 may comprise a threaded member, e.g., a screw, that can be tightened and loosened with respect to an external object configured to receive the threaded member. A flexible or bendable portion 812 positioned between the first and second ends 808, 810 can allow movement, e.g., bending, of the second end 810 toward and away from the front surface 802. As shown in FIG. 8B, the bendable portion 812 may define an indent such that it has a smaller width compared to the remainder of the first coupling member 806, thereby configuring the bendable portion 812 to bend or flex in response to manual force applied to the second end 810 in the direction of the solid arrow. In some examples, the bendable portion 812 may comprise a joint or hinge, which can allow movement of the second end without bending or flexing the material constituting the first coupling member 806. To secure or lock the second end 810 of the first coupling member 806 to the front surface 802 of the manipulation member 800, a projection 811 can be included on the backside of the first coupling member 806. The projection 811 can be insertable into an aperture 814 shown in FIG. 8C, which may define a through-hole or may extend through only a portion of the total thickness of the manipulation member 800. In examples, the projection 811 may snap into place when urged into the aperture 814, thereby reversibly locking the projection 811, and thus the second 810 of the first coupling member 806, to the body 801 of the manipulation member 800. One or more objects, e.g., a portion of the patient's gown, can be positioned between the first coupling member 806 and the front surface 802 of the manipulation member 800 prior to inserting the projection 811 into the aperture 814, such that upon locking, the manipulation member 800 is secured to such objects.

As further shown in FIG. 8B, the manipulation member 800 can include a second coupling member 816, which may comprise an arcuate clip in some examples, configured to attach to various objects, such as a patient gown or a piece of operating equipment. The second coupling member 816 can include a first end 818 attached or integrally formed with a back surface 820 of the manipulation member 800, and a free end 822 configured to move away from the back surface 820 in response to an object, e.g., patient gown, wristband, instrument tray, etc., being forced underneath the second coupling member 816 in the direction of the dashed arrow. To accommodate objects in this manner, the second coupling member 816 can comprise one or more materials configured to slightly bend or flex. The greater the flexibility of the second coupling member 816, the larger the objects it can accommodate. Like the first coupling member 806, the second coupling member 816 may additionally or alternatively comprise a joint or hinge configured to allow movement of the free end 822.

The shape and dimensions of the manipulation member 800 may vary. In some examples, the width (w) may range from about 1.5 cm to about 3.5 cm, about 2 cm to about 3 cm, about 2.25 cm to about 2.75 cm, or about 2.5 cm. In additional embodiments, e.g., to accommodate various guide extension catheters, the width may be less than 1.5 cm or greater than 3.5 cm, for example up to 4, 5, 6, or 8 cm or more. The length (l) may range from about 6 cm to about 10 cm, about 7 cm to about 9 cm, about 7.5 cm to about 8.5 cm, or about 8 cm or more. The length may also vary such that values below 6 cm and above 10 cm are also within the scope of this disclosure. The thickness (t) of the body 801 of the manipulation member 800 may range from about 2 mm to about 8 mm, about 3 mm to about 6 mm, about 3.5 mm to about 5 mm, or about 4 mm. The thickness may be less than 2 mm or greater than 8 mm in some examples, for instance depending on the materials comprising the manipulation member 800.

In some examples, the manipulation member 800 may be weighted, such that coupling, e.g., clipping, it to an object may be unnecessary to secure a guide extension catheter in place during a medical procedure. According to such examples, the manipulation member 800 may have a weight that resists movement of the guide extension catheter to which it is attached or formed with when the manipulation member 800 is simply rested, i.e., not attached, on a surface external to a patient. Embodiments may also involve coupling the manipulation member 800 to an object, even if the manipulation member 800 is weighted, thereby providing multiple securing means to ensure that the guide extension catheter remains stationary once it is positioned as desired. The specific weight of the manipulation member 800 may vary, provided it weighs at least as much as the guide extension catheter. In various embodiments, the weight of the manipulation member 800 may range from about 1 oz. to about 10 oz., about 1.5 oz. to about 8 oz., about 2 oz. to about 6 oz., about 2.5 oz. to about 4 oz., or about 3 oz. to about 3.5 oz. In some embodiments, the majority of the weight of the manipulation member 800 may be concentrated in one or more portions thereof. For instance, the first coupling member 806 may be weighted heavily relative to the body 801 and/or the second coupling member 816. In additional examples, the second coupling member 816 may be weighted heavily relative to the body 801 and/or the first coupling member 806. In other examples, the weight may be distributed approximately evenly throughout the manipulation member 800 or the body 801.

The configuration of the first and/or second coupling members 806, 816 may vary. For example, either or both coupling members 806, 816 can comprise a spring-loaded clip, a slidable pin, or various adhesives, e.g., Velcro, glue, tape, etc., configured to couple the manipulation member 800 to various objects. In some embodiments, the shape of the manipulation member 800 may provide the coupling mechanism. For instance, the manipulation member 800, in whole or in part, may be inserted into and secured within an aperture or slot configure to reversibly lock, e.g., snap, the manipulation member 800 in place. Such examples may include one or more components configured to lock the manipulation member 800 within the receiving aperture. For example, the manipulation member 800 and/or the aperture may include a biased latch, pin, or ball configured to lock and unlock the manipulation member 800 in response to a user pushing or pulling, respectively, the manipulation member 800 into and out of the aperture. In some embodiments, the manipulation member 800 may include a tong-like mechanism configured to reversibly grasp objects of various sizes. Such a mechanism may extend proximally, and may be biased, e.g., via a spring, toward the closed position, such that the user may open the mechanism manually and release the mechanism around an object to be grasped. In some examples, at least one or more portions of the manipulation member 800 may be magnetic, such that the manipulation member 800 can be secured to various objects attracted to magnets, including ferromagnetic and paramagnetic objects comprised of various metals. Magnetism may constitute the sole or supplemental securing means of the manipulation member 800.

The shape of the manipulation member 800 can vary. For example, the body 801 may be approximately oval-shaped, as shown in FIGS. 8A-8C, or it may be approximately rectangular, triangular, circular, oblong, or cylindrical. The manipulation member 800 may also define one or more ergonomic surfaces configured to match the manual grip of a user and guide consistent manual engagement therewith. Depending on its specific configuration, the manipulation member 800 may be of unitary construction, or it may include two or more distinct components coupled to form a singular device.

FIG. 9A illustrates an example reinforcement member 900, which may be included in some embodiments to increase the stiffness of the elongate tube member 902 of a guide extension catheter (only a portion of which is shown). As described above, the reinforcement member 900 may be sandwiched between two polymer layers constituting the elongate tube member 902. The reinforcement member 900 can include a plurality of longitudinal bars or strips 904, which may be interlaced with one or more cross-bars or strips 906. The strips 904, 906 may be arranged perpendicularly, or substantially perpendicularly, with respect to each other, or they may be diagonally arranged. In some examples, only the longitudinal or the cross strips may be included. The reinforcement member 900 can extend around the entire perimeter of the elongate tube member 902, or only a portion thereof.

FIG. 9B illustrates another example reinforcement member 908 included with an elongate tube member 910 (only a portion of which is shown). In this example, the reinforcement member 908 can be comprised of spiraling bars or strips 912, 914, which may crisscross. In embodiments, strips in only one spiral direction, i.e., 912 or 914, may be included. Any suitable angle or combination of angles of the spiral with respect to the longitudinal axis of the tube may be used. Like reinforcement member 900, reinforcement member 908 can be sandwiched between individual layers constituting the elongate tube member 910. The particular configuration of the reinforcement member, its location and/or length may vary in different embodiments of the guide extension catheters disclosed herein, which are not confined to examples including reinforcement members, or specific embodiments thereof. The materials constituting the reinforcement member may also vary. In examples, the reinforcement member can include stainless steel, a platinum alloy, and/or one or more polymers, for instance.

EXAMPLES

The above Detailed Description is intended to be illustrative and not restrictive. The above-described embodiments (or one or more features or components thereof) can be used in varying combinations with each other unless clearly stated to the contrary. Other embodiments can be used, such as by one of ordinary skill in the art upon reviewing the above Detailed Description. Also, various features or components have been grouped together to streamline the disclosure. This should not be interpreted as intending that an unclaimed disclosed feature is essential to any claim. Rather, inventive subject matter can lie in less than all features of a particular disclosed embodiment. Thus, the following claim examples are hereby incorporated into the Detailed Description, with each example standing on its own as a separate embodiment.

In Example 1, a guide extension catheter for use with a predefined length guide catheter including a continuous lumen having a cross-sectional inner diameter can include an elongate tube member, a push member, and a manipulation member. The tube member can have a circular cross-section with a cross-sectional outer diameter sized to be insertable through the cross-sectional inner diameter of the guide catheter's continuous lumen and can define a coaxial lumen having a cross-sectional inner diameter through which an interventional cardiology device is insertable. The push member can be rigid enough to allow the tube member to be advanced through the guide catheter. The push member can be proximal of, operably connected to, and more rigid along a longitudinal axis than the tube member. The push member can have a maximal cross-sectional dimension at a proximal portion that is smaller than the cross-sectional outer diameter of the tube member and can have a length that, when combined with the length of the tube member, is longer than the guide catheter, such that when at least a distal portion of the tube member is extended distally of a distal end of the guide catheter, at least a portion of the proximal portion of the push member extends proximally through a hemostatic valve in common with the interventional cardiology device insertable through the coaxial lumen of the tube member. The manipulation member can be coupled to the push member and configured to secure the guide extension catheter in place during use.

In Example 2, the guide extension catheter of Example 1 can optionally be configured such that the manipulation member is coupled to a proximal end of the push member.

In Example 3, the guide extension catheter of any one of Examples 1 or 2 can optionally be configured such that the manipulation member comprises at least one coupling member configured to attach to at least a portion of an external object.

In Example 4, the guide extension catheter of Example 3 can optionally be configured such that the at least one coupling member comprises a flexible clip or a clamp configured to receive and grasp the external object.

In Example 5, the guide extension catheter of Example 3 can optionally be configured such that the at least one coupling member comprises a tab that includes a first end and a second end, the first end fixed to a body of the manipulation member and the second end releasably engageable with the body of the manipulation member.

In Example 6, the guide extension catheter of Example 5 can optionally be configured such that the tab further comprises a flexible portion between the first end and the second end.

In Example 7, the guide extension catheter of any one of Examples 5 or 6 can optionally be configured such that the second end of the tab is configured to releasably engage the body of the manipulation member via a projection extending from a surface of the tab and insertable within an aperture defined by the body of the manipulation member.

In Example 8, the guide extension catheter of any one or any combination of Examples 1-7 can optionally be configured such that the manipulation member weighs at least as much as the tube member and the push member, combined.

In Example 9, the guide extension catheter of any one or any combination of Examples 1-8 can optionally be configured such that the manipulation member weighs about 1 oz. to about 8 oz., inclusive.

In Example 10, the guide extension catheter of any one or any combination of Examples 1-9 can optionally be configured such that the tube member includes a flexible cylindrical distal tip portion and a flexible cylindrical portion with a reinforcement member that is proximal to the flexible cylindrical distal tip portion. A distal portion of the tube member can be more flexible than a proximal portion of the tube member.

In Example 11, the guide extension catheter of any one or any combination of Examples 1-10 can optionally be configured such that the tube member comprises an inner polymer layer and an outer polymer layer.

In Example 12, the guide extension catheter of any one or any combination of Examples 1-11 can optionally be configured such that the proximal portion of the tube member further comprises structure defining a proximal side opening extending for a distance along the longitudinal axis, and accessible from a longitudinal side defined transverse to the longitudinal axis, to receive the interventional cardiology device into the coaxial lumen while the proximal portion remains within the continuous lumen of the guide catheter.

In Example 13, the guide extension catheter of Example 12 can optionally be configured such that the proximal side opening defines a concave track configured to guide the interventional cardiology device along a length of the concave track.

In Example 14, the guide extension catheter of any one or any combination of Examples 1-13 can optionally be configured such that the interventional cardiology device insertable through the coaxial lumen is a stent, a stent catheter, or a balloon catheter.

In Example 15, a method can comprise advancing a distal end of a guide catheter having a continuous lumen through a blood vessel to an ostium of a coronary artery; advancing a distal end of a guide extension catheter through, and beyond the distal end of, the guide catheter, including advancing a push member of the guide extension catheter that is proximal of, operably connected to, and more rigid along a longitudinal axis than an elongate tube member of the guide extension catheter, into the continuous lumen of the guide catheter, the push member having a maximal cross-sectional dimension at a proximal portion that is smaller than a cross-sectional outer diameter of the tube member and having a length such that, when combined with the length of the tube member, a distal end portion of the tube member is extendable through the continuous lumen of the guide catheter and beyond the distal end of the guide catheter while a proximal end of the push member is extendable through a hemostatic valve positioned at a proximal end of the guide catheter, the advancement of the push member causing advancement of the distal end portion of the tube member beyond the distal end of the guide catheter while a side opening of the guide extension catheter remains within the continuous lumen of the guide catheter, the side opening extending for a distance along a longitudinal axis of the guide extension catheter and accessible from a longitudinal side defined transverse to the longitudinal axis, the tube member defining a lumen coaxial with the continuous lumen of the guide catheter and having a cross-sectional inner diameter through which an interventional cardiology device is insertable; maintaining the distal end portion of the tube member of the guide extension catheter beyond the distal end of the guide catheter by securing a manipulation member at a position external to the hemostatic valve, the manipulation member coupled to the proximal portion of the push member; and while maintaining the distal end portion of the tube member positioned beyond the distal end of the guide catheter, advancing a balloon catheter or stent through the hemostatic valve and into the continuous lumen of the guide catheter, into the side opening and through the coaxial lumen of the tube member, and into the coronary artery.

In Example 16, the method of Example 15 can optionally be configured such that securing the manipulation member excludes manually holding the manipulation member.

In Example 17, the method of any one of Examples 15 or 16 can optionally be configured such that securing the manipulation member involves receiving and grasping an external object via a coupling member of the manipulation member.

In Example 18, the method of Example 17 can optionally be configured such that the coupling member comprises a flexible clip, a clamp, or a tab.

In Example 19, the method of any one or any combination of Examples 15-18 can optionally be configured such that the manipulation member weighs at least as much as the push member and the tube member combined, and securing the manipulation member comprises placing it on a surface.

In Example 20, the method of any one or any combination of Examples 15-19 can optionally be configured such that the manipulation member weighs about 1 oz. to about 8 oz., inclusive.

In Example 21, the method of any one or any combination of Examples 15-20 can optionally be configured such that the tube member includes a flexible cylindrical distal tip portion and a flexible cylindrical portion with a reinforcement member that is proximal to the flexible cylindrical distal tip portion. A distal portion of the tube member can be more flexible than a proximal portion of the tube member.

In Example 22, the guide extension catheter or method of any one or any combination of Examples 1-21 can optionally be configured such that all components or options recited are available to use or select from.

CLOSING NOTES

The above Detailed Description includes references to the accompanying drawings, which form a part of the Detailed Description. The Detailed Description should be read with reference to the drawings. The drawings show, by way of illustration, specific embodiments in which the present guide extension catheters and related methods can be practiced. These embodiments are also referred to herein as "examples."

Certain terms are used throughout this patent document to refer to particular features or components. As one skilled in the art will appreciate, different people may refer to the same feature or component by different names. This patent document does not intend to distinguish between components or features that differ in name but not in function. For the following defined terms, certain definitions shall be applied unless a different definition is given elsewhere in this patent document. The terms "a," "an," and "the" are used to include one or more than one, independent of any other instances or usages of "at least one" or "one or more." The term "or" is used to refer to a nonexclusive or, such that "A or B" includes "A but not B," "B but not A," and "A and B." All numeric values are assumed to be modified by the term "about," whether or not explicitly indicated. The term "about" refers to a range of numbers that one of skill in the art considers equivalent to the recited value (i.e., having the same function or result). In many instances, the term "about" can include numbers that are rounded to the nearest significant figure. The recitation of numerical ranges by endpoints includes all numbers and sub-ranges within and bounding that range (e.g., 1 to 4 includes 1, 1.5, 1.75, 2, 2.3, 2.6, 2.9, etc. and 1 to 1.5, 1 to 2, 1 to 3, 2 to 3.5, 2 to 4, 3 to 4, etc.). The terms "patient" and "subject" are intended to include mammals, such as for human or veterinary applications. The terms "distal" and "proximal" are used to refer to a position or direction relative to an operating physician. "Distal" and "distally" refer to a position that is distant from, or in a direction away from, the physician. "Proximal" and "proximally" refer to a position that is near, or in a direction toward, the physician. And the term "interventional device(s)" is used to include, but is not limited to, guidewires, balloon catheters, stents and stent catheters.

The scope of the present guide extension catheters and methods should be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended; that is, a device or method that includes features or components in addition to those listed after such a term in a claim are still deemed to fall within the scope of that claim. Moreover, in the following claims, the terms "first," "second" and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. A guide extension catheter for use with a predefined length guide catheter including a continuous lumen having a cross-sectional inner diameter, the guide extension catheter comprising:

an elongate tube member having a circular cross-section having a cross-sectional outer diameter sized to be insertable through the cross-sectional inner diameter of the guide catheter's continuous lumen and defining a coaxial lumen having a cross-sectional inner diameter through which an interventional cardiology device is insertable;

a push member that is rigid enough to allow the tube member to be advanced through the guide catheter, the push member being proximal of and operably connected to the elongate tube, the push member having a maximal cross-sectional dimension at a proximal portion that is smaller than the cross-sectional outer diameter of the tube member and having a length that, when combined with the length of the tube member, is longer than the guide catheter, such that when at least a distal portion of the tube member is extended distally of a distal end of the guide catheter, at least a portion of the proximal portion of the push member extends proximally through a hemostatic valve in common with the interventional cardiology device insertable through the coaxial lumen of the tube member; and a manipulation member coupled to the push member, the manipulation member including means for securing its position during use in the absence of manual holding by a user.

2. The guide extension catheter of claim 1, wherein the manipulation member is coupled to a proximal end of the push member.

3. The guide extension catheter of claim 1, wherein the means for securing the manipulation member comprises at least one coupling member configured to attach to at least a portion of an external object.

4. The guide extension catheter of claim 3, wherein the at least one coupling member comprises a flexible clip or a clamp configured to receive and grasp the external object.

5. The guide extension catheter of claim 3, wherein the at least one coupling member comprises a tab that includes a first end and a second end, the first end fixed to a body of the manipulation member and the second end releasably engageable with the body of the manipulation member.

6. The guide extension catheter of claim 5, wherein the tab further comprises a flexible portion between the first end and the second end.

7. The guide extension catheter of claim 5, wherein the second end of the tab is configured to releasably engage the body of the manipulation member via a projection extending from a surface of the tab and is insertable within an aperture defined by the body of the manipulation member.

8. The guide extension catheter of claim 1, wherein the means for securing the manipulation member comprising weighting the manipulation member at least as much as the tube member and the push member, combined.

9. The guide extension catheter of claim 8, wherein the manipulation member weighs about 1 oz. to about 8 oz., inclusive.

10. The guide extension catheter of claim 1, wherein the tube member includes a flexible cylindrical distal tip portion and a flexible cylindrical portion with a reinforcement member that is proximal to the flexible cylindrical distal tip portion, and wherein a distal portion of the tube member is more flexible than a proximal portion of the tube member.

11. The guide extension catheter of claim 1, wherein the proximal portion of the tube member further comprises structure defining a proximal side opening extending for a distance along a longitudinal axis, and accessible from a longitudinal side defined transverse to the longitudinal axis, to receive the interventional cardiology device into the coaxial lumen while the proximal portion is located within the continuous lumen of the guide catheter.

12. The guide extension catheter of claim 11, wherein the proximal side opening defines a concave track configured to guide the interventional cardiology device along a length of the concave track.

13. The guide extension catheter of claim 1, wherein the interventional cardiology device insertable through the coaxial lumen is a stent, a stent catheter, or a balloon catheter.

14. A method comprising:

advancing a distal end of a guide catheter having a continuous lumen through a blood vessel to an ostium of a coronary artery;

advancing a distal end of a guide extension catheter through, and beyond the distal end of, the guide catheter, including advancing a push member of the guide extension catheter, that is proximal of and operably connected to a tube member of the guide extension catheter, into the continuous lumen of the guide catheter, the push member having a maximal cross-sectional dimension at a proximal portion that is smaller than a cross-sectional outer diameter of the tube member and having a length such that, when combined with the length of the tube member, a distal end portion of the tube member is extendable through the continuous lumen of the guide catheter and beyond the distal end of the guide catheter while a proximal end of the push member is extendable through a hemostatic valve positioned at a proximal end of the guide catheter, the advancement of the push member causing advancement of the distal end portion of the tube member beyond the distal end of the guide catheter while a side opening of the guide extension catheter is positioned within the continuous lumen of the guide catheter, the side opening extending for a distance along a longitudinal axis of the guide extension catheter and accessible from a longitudinal side defined transverse to the longitudinal axis, the tube member defining a lumen coaxial with the continuous lumen of the guide catheter and having a cross-sectional inner diameter through which an interventional cardiology device is insertable;

securing a manipulation member at a position external to the hemostatic valve, the manipulation member coupled to the proximal portion of the push member; and while maintaining the distal end portion of the tube member positioned beyond the distal end of the guide catheter, advancing a balloon catheter or stent through the hemostatic valve and into the continuous lumen of the guide catheter, into the side opening and through the coaxial lumen of the tube member, and into the coronary artery.

15. The method of claim 14, wherein securing the manipulation member excludes manually holding the manipulation member.

16. The method of claim 14, wherein securing the manipulation member involves receiving and grasping an external object via a coupling member of the manipulation member.

17. The method of claim 16, wherein the coupling member comprises a flexible clip, a clamp, or a tab.

18. The method of claim 14, wherein the manipulation member weighs at least as much as the push member and the tube member combined, and wherein securing the manipulation member comprises placing it on a surface.

19. The method of claim 18, wherein the manipulation member weighs about 1 oz. to about 8 oz., inclusive.

20. The method of claim 14, wherein the tube member includes a flexible cylindrical distal tip portion and a flexible cylindrical portion with a reinforcement member that is proximal to the flexible cylindrical distal tip portion, and wherein a distal portion of the tube member is more flexible than a proximal portion of the tube member.

* * * * *